United States Patent
Beebe et al.

(10) Patent No.: US 8,124,410 B2
(45) Date of Patent: Feb. 28, 2012

(54) METHODS OF FINDING, SELECTING AND STUDYING CELLS IN HETEROGENEOUS CO-CULTURES

(75) Inventors: David James Beebe, Monona, WI (US); Hongmei Yu, Madison, WI (US); Caroline Alexander, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 431 days.

(21) Appl. No.: 11/449,344

(22) Filed: Jun. 8, 2006

(65) Prior Publication Data

US 2007/0287178 A1 Dec. 13, 2007

(51) Int. Cl.
*C12N 5/02* (2006.01)
(52) U.S. Cl. .................. 435/383; 435/347; 435/381
(58) Field of Classification Search .................. None
See application file for complete search history.

(56) References Cited

U.S. PATENT DOCUMENTS

| | | | | |
|---|---|---|---|---|
| 4,729,955 A | * | 3/1988 | Kodama et al. | 435/183 |
| 5,858,721 A | * | 1/1999 | Naughton et al. | 435/69.1 |
| 6,440,734 B1 | * | 8/2002 | Pykett et al. | 435/372 |
| 6,495,161 B1 | * | 12/2002 | Soon-Shiong et al. | 424/451 |
| 6,562,616 B1 | * | 5/2003 | Toner et al. | 435/293.1 |

OTHER PUBLICATIONS

U.S. Appl. No. 10/839,916, filed May 6, 2004, Lowery, et al.
Atencia J & Beebe D, "Controlled microfluidic interfaces," Nature 437:648-655 (2005).
Kordon E & Smith G, "An entire functional mammary gland may comprise the progeny from a single cell," Development. 125:1921-1930 (1998).
Rizvi A & Wong M, "Epithelial stem cells and their niche: there's no place like home," Stem Cells 23:150-165 (2005).
Walker G, et al., "Microenvironment design considerations for cellular scale studies," Lab. Chip. 4:91-97 (2004).
Yu H, et al., "Diffusion dependent cell behavior in microenvironments," Lab. Chip. 5:1089-1095 (2005).

* cited by examiner

*Primary Examiner* — Jim Ketter
(74) *Attorney, Agent, or Firm* — Quarles & Brady LLP

(57) ABSTRACT

Co-cultures of heterogeneous cell populations in a diffusion-constrained microenvironment and methods for co-culturing are disclosed.

19 Claims, No Drawings

METHODS OF FINDING, SELECTING AND STUDYING CELLS IN HETEROGENEOUS CO-CULTURES

STATEMENT REGARDING FEDERALLY SPONSORED RESEARCH OR DEVELOPMENT

This invention was made with United States government support awarded by the Army (ARMY W81XWH-04-1-0572). The United States Government has certain rights in this invention.

CROSS-REFERENCE TO RELATED APPLICATIONS

Not applicable.

BACKGROUND

In vivo, cells are maintained in three-dimensional microenvironments regulated by physical, chemical and biological factors. The microenvironments are characterized by (1) a short distance between cells, (2) a continuous nutrient supply and waste removal, (3) a common set-point temperature, and (4) a minimal stress level. On the other hand, conventional cell culture systems in which cells are grown in monolayers in flasks or in dishes substitute only imperfectly for such microenvironments. For example, convection, or bulk fluid movement, is increased and can bring about undesired variation in temperature, solute concentration, dissolved gas concentration and can lead to surface tension differences at a gas-solution interface (i.e., Marangoni effect). Such variations cause mixing, as opposed to diffusion, of molecules secreted by cells in the culture. Consequently, secreted molecules rapidly distribute over the entire volume of the culture, interfering with both autocrine and paracrine signaling that is associated in vivo with cell-cell interactions. Additionally, three-dimensional cell growth does not take place in conventional cell culture environments, as cell-to-cell contact is largely absent.

In the past decade, research has shown that factors such as surface tension, energy dissipation and associated convective flow, and fluidic resistance affect the behavior of fluids in conventional cell culture, whereas these factors can be attenuated by providing suitable microenvironments. The field of microfluidics studies how these behaviors affect culture systems, and how they can be worked around or exploited for new uses, particularly for cell culture systems having a size scale that provides environments for cells that are more similar to their native in vivo culture environments than those of conventional culture systems.

Microfluidic systems can be restrict flow such that small molecules move in the culture only via diffusion (i.e., essentially convection-free). Because microenvironments are so small, gas-liquid interfaces can be eliminated. As such, convection-free in vitro microenvironments offer opportunities to study cellular processes such as autocrine and paracrine functions that cannot readily be studied in conventional systems. A related advantage of microfluidics is that microenvironments can enhance desirable cell-to-cell contact.

As culture systems are scaled down, factors such as diffusion, surface tension and viscosity become important. The skilled artisan is familiar with such factors, which are summarized, e.g., in Atencia J & Beebe D, "Controlled microfluidic interfaces," Nature 437:648-655 (2005); Walker G, et al., "Microenvironment design considerations for cellular scale studies," Lab. Chip. 4:91-97 (2004); Yu H, et al., "Diffusion dependent cell behavior in microenvironments," Lab. Chip. 5:1089-1095 (2005); and U.S. Published Patent Application No. 2004/0259177, each of which is incorporated herein by reference as if set forth in its entirety.

Although embryonic stem cells have been cultured and monitored in microenvironmental systems, long-term study of cell proliferation is largely unexplored. Isolation and in vitro culturing of adult stem cells remain unsatisfactory. Rizvi A & Wong M, "Epithelial stem cells and their niche: there's no place like home," Stem Cells 23:150-165 (2005), incorporated herein by reference as if set forth in its entirety. Current techniques for isolating adult stem cells include identifying cell surface markers and functional studies (e.g., dye efflux and patch clamping), whereas current techniques for culturing adult stem cells utilize macroenvironments.

Likewise, isolation and in vitro culturing of many primary cells, such heterogeneous primary epithelial cells, remain unsatisfactory. In fact, most primary cells die when transferred to primary culture. Any cell lines that emerge from such culture typically reflect a small subpopulation with a low frequency of mutation that permits genetic adaptation to non-physiological culture conditions. Consequently, karyotypes of the resulting cell lines are so abnormal that such cells would not survive in vivo when used for transplant.

For the foregoing reasons, there is a need for microfluidics methods and systems for evaluating co-cultures of heterogeneous cells, as well as the factors that influence proliferation.

BRIEF SUMMARY

It has not previously been observed that heterogeneous primary cell populations can support cell growth in a co-culture microenvironment in which substantially all movement of components in the environment is by diffusion (hereinafter a "diffusion-constrained microenvironment"). This observation further suggests that heterogeneous cell populations co-cultured in in vitro microenvironments can provide controlled environmental stimuli to such cells which are sufficient to permit the cells to proliferate as they would in vivo. Further, it is also possible to provide to the cultures various factors that modulate proliferation of the cultured cells.

In a first aspect, the present invention is summarized in that a method of co-culturing heterogeneous cell populations includes the step of co-culturing cells the cells in a diffusion-constrained microenvironment. In a related aspect, at least a sub-population of the co-cultured cells can proliferate in the microenvironment and the proliferation can be monitored or observed. The ability to monitor and assess proliferative capacity of cells in the microenvironment permits one to avoid prior reliance upon serial transplant studies of the type described in Kordon E & Smith G, "An entire functional mammary gland may comprise the progeny from a single cell," Development. 125:1921-1930 (1998), incorporated herein by reference as if set forth in its entirety and also permits controlled co-culture of sub-populations that facilitate proliferation, either by cell-to-cell contact or by secretion of soluble factors.

The heterogeneous cell type populations co-cultured in the diffusion-constrained microenvironment can derive from a single source (e.g., primary cells obtained from a tissue explant) or from a plurality of sources, and can, but need not necessarily, include selected subpopulations having one or more ascertainable attributes. The subpopulations can be selected, e.g., by sorting a population on the basis of a cell surface marker or other feature, by selectively depleting cells from a population, or by any other method for obtaining a subpopulation of interest. The heterogeneous cells in co-culture can be in cell-to-cell contact, or can be spaced apart. This permits one to determine an effect of one cell population (e.g., a growth-promoting cell) upon another (e.g., a cell having proliferative capacity) and to determine whether the effect is mediated by cell-to-cell contact or by interaction of one cell population with a soluble factor secreted from another cell population in the diffusion-constrained microenvironment.

In another aspect, the present invention is summarized in that the co-culture methods enable one to determine the proliferative requirements of the proliferating cells or to determine the contributions of other non-proliferative cells in the co-culture to the observed proliferation.

In some embodiments, the co-cultured heterogeneous cells are primary cells, such as primary epithelial or stromal cells. Factors that promote proliferation can be supplied by cells in contact with the cells having proliferative capacity, by cells that secrete one or more soluble factors that signal division of the cells having proliferative capacity, or by adding into the co-culture one or more soluble factors that can diffuse into contact with the cells having proliferative capacity.

In some embodiments, the numbers of cells seeded can range between about 150 cells per culture to about 1500 cells per culture or more, although these numbers will vary with the ability of the culture to support very small or very large numbers of cells, as well as with the concentration of proliferative cells in a sample, and the proliferative capacity of such cells. The number of seeded cells can directly affect proliferative capacity in the co-culture, in that, e.g., at low cell number an essential cell type or secreted growth-promoting agent may be present in insufficient quantity or absent from the culture, or may not contact the cells having proliferative capacity. The skilled person will appreciate that evaluation of the proliferative capacity in co-cultures seeded at various cell densities will suggest further inquiry for determining the cell types and signaling mechanisms important to proliferation, as well as for determining the attributes of the cells having proliferative capacity.

In some embodiments, the primary culture is obtained prior to or after a treatment for a condition or disease characterized by the presence of proliferating cells, such as a cancer. In such embodiments, the method can include steps for determining the effect of a treatment upon the proliferative capacity in an affected tissue. Such steps can include, but are not limited to, cell counting methods and immunocytochemistry, as are known to the skilled artisan or are disclosed elsewhere herein.

The described embodiments of the present invention have many advantages, including the ability to direct and evaluate physical, chemical and biological interactions between cells (as well as interactions between cells and other agents or factors) in a controlled environment. The systems described permit co-culturing of cells including adult stem cells (e.g., epithelial stem cells) from primary cultures, which cells may not be present in sufficiently large quantity, or may not encounter sufficient cell-cell interactions or other signals, to be successfully cultured in traditional culture methods.

A second advantage of the present invention is that it avoids the need for costly and time-consuming transplantation of cultured cells into a host in vivo to ascertain whether proliferation is occurring in a culture.

A third advantage of the present invention is that molecular gradients of test agents or compounds known to be secreted by various cell types (or to which it is desired to expose the co-cultured cell(s)) can be established in the microenvironment, thereby facilitating analysis of the effects of various agents or compounds on primary cell cultures. The test agents or compounds can positively or negatively affect, without limitation, the growth-promoting cell(s), the cell(s) having proliferative capacity, or any other cell in the co-culture. For example, the agents or compounds can cause cells to increase or decrease their growth-promoting activity, or to increase or decrease responsiveness to the growth-promoting activity, and can selectively eliminate cells or enrich cell populations in the co-culture.

These and other features, aspects and advantages of the present invention will become better understood from the description that follows. The description of preferred embodiments is not intended to limit the invention to cover all modifications, equivalents and alternatives. Reference should therefore be made to the claims herein for interpreting the scope of the invention.

BRIEF DESCRIPTION OF THE DRAWINGS

Not applicable.

DESCRIPTION OF PREFERRED EMBODIMENTS

The construction of devices with microenvironments for cell culture are known to the skilled artisan. An important consideration in the construction of devices with microenvironments is its dimensions. Previous studies have shown that the height, as opposed to the length or the width, of a microchannel has a profound effect on proliferation rates. Yu et al., supra.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are now described.

As used herein, "co-culture" refers to a heterogeneous cell culture or a tissue culture made by transfer from a natural source to an artificial medium. A co-culture of primary cells may be obtained either by allowing cells to migrate out from a tissue adhering to a suitable substrate or by disaggregating a tissue mechanically or enzymatically to produce a suspension of heterogeneous cells.

As used herein, "proliferative cell" refers to any cell having the ability to proliferate in the provided culture conditions. It is also contemplated that a "cell having proliferative capacity" can be a cell that is dividing and has a normal karyotype, such as primary cells.

The invention will be more fully understood upon consideration of the following non-limiting Examples.

EXAMPLES

Example 1

Culturing Mammary Gland Primary Epithelial Cells

Methods: Primary mouse mammary gland epithelial cells from fourteen-week-old Balb/C mice were seeded in separate microchannels having constant length, width and height ($20 \times 10 \times 0.25$ mm$^3$; see Yu, et al., supra) coated with Matrigel- (BD Biosciences; San Jose, CA) at a cell density of 150, 350, 750, or 1500 cells/channel in DMEM (Sigma Aldrich; St. Louis, MO) medium supplemented with 5 µg/ml insulin and 10 ng/ml EGF in a humidified incubator. Nine microchannels were seeded for each cell density.

The medium in the microchannels was renewed each day. On each of three successive days, three microchannels at each cell concentration were washed with PBS, fixed with 4% PFA and stored at 4° C. After three days of culture, all microchannels were collected, washed with water, stained with 20 µg/ml of Hoechst 33342 for 5 minutes, and then examined by fluorescence microscopy. Each microchannel was scanned automatically, and images were captured. Nucleus counts and total cell area was obtained using MetaMorph Imaging System (Universal Imaging Corp.; West Chester, Pa.).

Results: The microchannel seeded with over 1500 cells had a significantly faster (~2x) growth rate than the microchannels seeded with 150, 350 or 750 cells. The channels containing over 1500 cells grew at a high rate, and channels with 300 cells grew at a low rate. Channels with intermediate numbers of cells had a bimodal growth pattern, that is, they grew either at the high rate or at the low rate. The bimodal growth pattern suggested that a rare growth-promoting cell was present or not, and that a frequency of such a cell was about 1/1500 in a mouse mammary gland. This frequency is consistent with the mammary stem cell frequency determined by in vivo transplantation. See Kordon & Smith, supra. The data suggest that cells secrete soluble factors into the medium that regulate the proliferation of other cells within the diffusion-constrained microchannels.

Example 2 (Prophetic)

Culturing Primary Cells Obtained from a Cancerous Tissue Sample

Methods: A first tissue sample is obtained by aseptic technique from a subject prior to a treatment effective to reduce the number of proliferative cells in a tissue isolated from a cancer patient. The sample is either disrupted mechanically (by pipetting or mincing) or digested enzymatically (e.g., either with trypsin or with collagenase) to obtain primary cells for seeding in Matrigel-coated microchannels. Cells are seeded and incubated at various cell densities (e.g., 150, 350, 750 and 1500 cells) into separate microchannels. Cell proliferation in the microchannels is monitored for one to three days as described elsewhere herein and a threshold number of seeded cells required to support proliferation is determined. The threshold number correlates with the number of proliferative cells in the sample.

A second tissue sample is obtained by aseptic technique from the subject after the treatment and cells are seeded in Matrigel-coated microchannels as described above at the same cell densities. As above, the number of seeded cells required to support proliferation is determined.

Results: A lower seeded cell density is required to support proliferation of the primary cells cultured in the microchannels before treatment than after treatment, indicating that the treatment is effective to reduce the number of growth-promoting cells in the tissue. For example, the number of cells required prior to treatment can be 150 cells, whereas the number of cells required for growth after treatment can be 1500.

The monitoring method described is advantageous in that it avoids the present need to determine the effectiveness of a treatment by transplanting primary cell cultures obtained before or after treatment into the bone marrow of a genetically distinct animal to ascertain the number (or density) of growth-promoting cells in the culture.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method of co-culturing heterogeneous cells in a culture comprising at least one growth-promoting cell and at least one cell having proliferative capacity, the method comprising the steps of:
    seeding the heterogeneous cells in a microchannel having constant length, width and height that defines a fluid microenvironment comprising components; and
    incubating the heterogeneous cells in the fluid microenvironment under conditions such that the components move in the entire culture only via diffusion for a time sufficient to proliferate the at least one proliferative cell.

2. A method as claimed in claim 1, wherein the heterogeneous cells derive from a single source.

3. A method as claimed in claim 2, wherein the single source is a culture of primary cells from a tissue.

4. A method as claimed in claim 3, wherein the culture of primary cells comprises cells that have migrated out of a tissue.

5. A method as claimed in claim 3, wherein the culture of primary cells comprises a suspension of cells from a tissue.

6. A method as claimed in claim 5, wherein the suspension is obtained by disaggregating a tissue.

7. A method as claimed in claim 5, wherein the suspension is obtained by digesting a tissue with an enzyme.

8. A method as claimed in claim 3, wherein the primary cell culture comprises cells selected from the group consisting of epithelial cells and stromal cells.

9. A method as claimed in claim 1, wherein different cell types of the heterogeneous cells derive from different sources.

10. A method as claimed in claim 9, wherein at least one source is primary cells from a tissue.

11. A method as claimed in claim 9, wherein at least one source is a cultured cell.

12. A method as claimed in claim 9, wherein at least one source is a selected cell sub-population.

13. A method as claimed in claim 1, wherein the at least one growth-promoting cell and the at least one cell having proliferative capacity are in cell-to-cell contact.

14. A method as claimed in claim 1, wherein the at least one growth-promoting cell and the at least one cell having proliferative capacity are spaced apart.

15. A method as claimed in claim 1, wherein the at least one cell having proliferative capacity is responsive to a soluble molecule secreted by the at least one growth-promoting cell.

16. A method as claimed in claim 1, wherein the method further comprises the step of introducing into the culture a soluble molecule that affects at least one cell type in the culture.

17. A method as claimed in claim 1, wherein the length is about 20 mm, the width is about 1 mm and the height is about 0.25 mm.

18. A method as claimed in claim 1, wherein different cell types of the heterogeneous cells derive from the same source.

19. A method as claimed in claim 1, wherein a single cell type of the heterogeneous cells derives from different sources.

* * * * *